(12) United States Patent
Fremy et al.

(10) Patent No.: US 10,563,236 B2
(45) Date of Patent: *Feb. 18, 2020

(54) METHOD FOR PRODUCING L-METHIONINE

(71) Applicant: ARKEMA FRANCE, Colombes (FR)

(72) Inventors: Georges Fremy, Sauveterre de Bearn (FR); Arnaud Masselin, Saint Malo (FR); Hugo Brasselet, Vallet (FR)

(73) Assignee: Akema France, Colombes (FR)

( * ) Notice: Subject to any disclaimer, the term of this patent is extended or adjusted under 35 U.S.C. 154(b) by 43 days.

This patent is subject to a terminal disclaimer.

(21) Appl. No.: 15/764,541

(22) PCT Filed: Sep. 29, 2016

(86) PCT No.: PCT/FR2016/052482
§ 371 (c)(1),
(2) Date: Mar. 29, 2018

(87) PCT Pub. No.: WO2017/055755
PCT Pub. Date: Apr. 6, 2017

(65) Prior Publication Data
US 2018/0282772 A1    Oct. 4, 2018

(30) Foreign Application Priority Data
Sep. 30, 2015    (FR) ...................................... 15 59278

(51) Int. Cl.
*C12P 13/12*    (2006.01)

(52) U.S. Cl.
CPC ....... *C12P 13/12* (2013.01); *C12Y 108/01007* (2013.01); *C12Y 108/01009* (2013.01); *C12Y 205/01049* (2013.01); *C12Y 112/01* (2013.01)

(58) Field of Classification Search
None
See application file for complete search history.

(56) References Cited

U.S. PATENT DOCUMENTS

| 3,636,098 | A | 1/1972 | Shima et al. |
| 4,657,856 | A | 4/1987 | Terada et al. |
| 5,493,058 | A | 2/1996 | Cadet et al. |
| 5,672,745 | A | 9/1997 | Hasseberg et al. |
| 5,990,349 | A | 11/1999 | Geiger et al. |
| 9,562,006 | B2 | 2/2017 | Fremy |
| 2009/0318715 | A1 | 12/2009 | Deck et al. |
| 2018/0291408 | A1* | 10/2018 | Fremy ............ C12Y 205/01049 |

FOREIGN PATENT DOCUMENTS

| EP | 0649837 | A1 | 4/1995 |
| FR | 2903690 | A1 | 1/2008 |
| WO | 9408957 | A1 | 4/1994 |
| WO | 2005107723 | A2 | 11/2005 |
| WO | 2007077041 | A1 | 7/2007 |
| WO | 2008006977 | A1 | 1/2008 |
| WO | 2008013432 | A1 | 1/2008 |
| WO | 2009043372 | A1 | 4/2009 |
| WO | 2010020290 | A1 | 2/2010 |
| WO | 2010020661 | A1 | 2/2010 |
| WO | 2013029690 | A1 | 3/2013 |
| WO | 2014033399 | A1 | 3/2014 |

OTHER PUBLICATIONS

International Search Report and Written Opinion for International Application No. PCT/FR2016/052482, dated Jan. 4, 2017, 8 pages.
Keire et al., "Kinetics and Equilibria of Thiol/disulfide Interchange Reactions of Selected Biological Thiols and Related Molecules with Oxidized Glutathione", The Journal of Organic Chemistry. vol. 57, No. 1, Jan. 1992, pp. 123-127.
Millis et at, "Oxidation/reduction potential of Glutathione", The Journal of Organic Chemistry, American Chemical Society, vol. 58, No. 15, Jan. 1993, pp. 4144-4146.
Chandrawati, R., et al., "Triggered Cargo Release by Encapsulated Enzymatic Catalysis in Capsosomes," Oct. 12, 2011, pp. 4958-4963, vol. 11, Nano Letters.
Nagai, S., et al., "{195c} Synthesis O-Acetylhomoserine," 1971, pp. 423-424, vol. 17, Part B, Methods in Enzymology.
Biller, K.A., et al, "Fermentation Hyperthermophiler Mikroorganismen am Beispiel von Pyrococcus Furiosus," Shaker Verlag, Maastricht/Herzogenrath, 2002, 145 pages.

\* cited by examiner

*Primary Examiner* — Anand U Desai
(74) *Attorney, Agent, or Firm* — RatnerPrestia

(57) ABSTRACT

Provided is an enzymatic process for preparing L-methionine from diethyl disulfide.

20 Claims, 2 Drawing Sheets

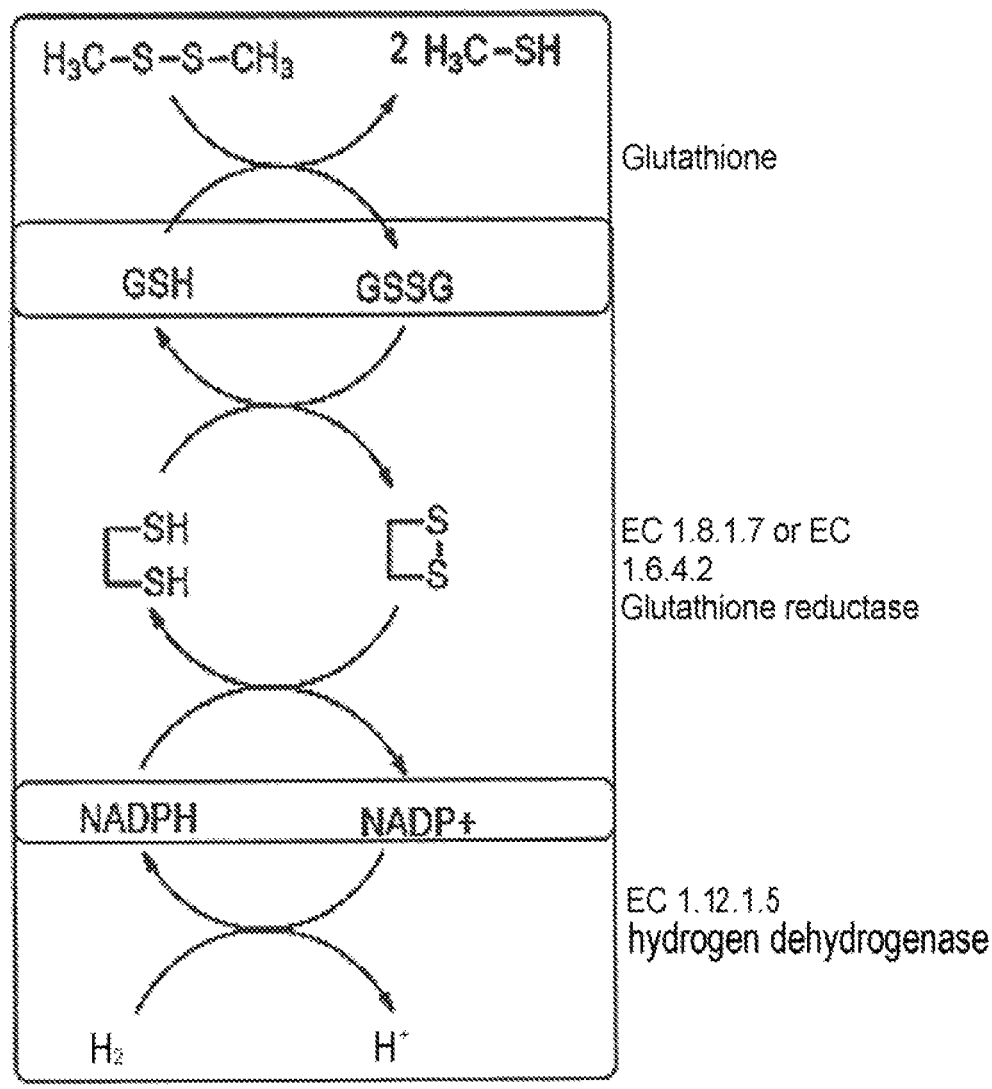
-- Figure 1 --

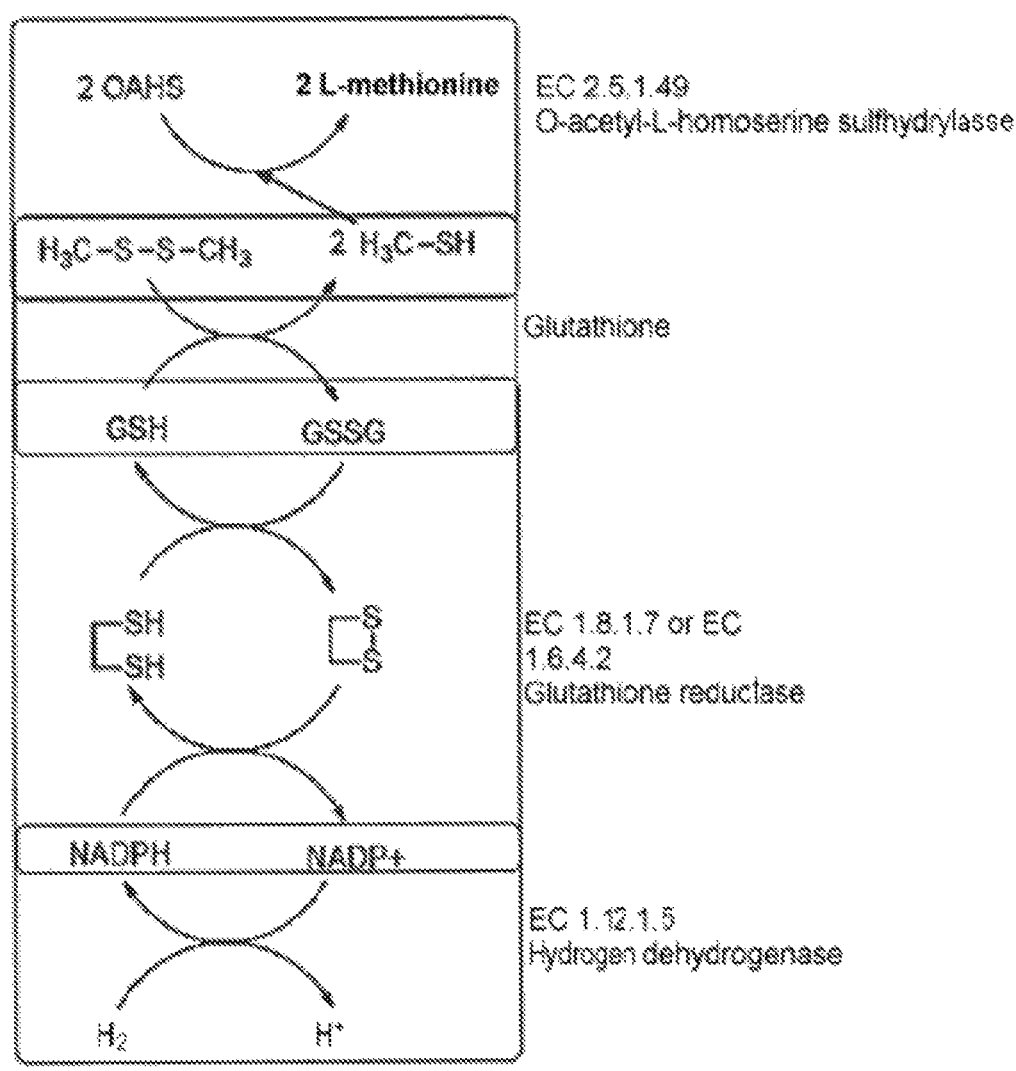
— Figure 2 —

METHOD FOR PRODUCING L-METHIONINE

CROSS-REFERENCE TO RELATED APPLICATIONS

This is the national phase of International Application No. PCT/FR2016/052482, filed 29 Sep. 2016, which claims priority to French Application No. 1559278, filed 30 Sep. 2015. The disclosure of each of these applications is incorporated herein by reference in its entirety for all purposes.

FIELD OF THE INVENTION

The present invention relates to a process for the production of L-Methionine by enzymatic reaction between an L-Methionine precursor, dimethyl disulfide (DMDS) and hydrogen. It also relates to a two-step process for the production of L-Methionine by enzymatic reaction between an L-Methionine precursor and methyl mercaptan, the latter being obtained by enzymatic hydrogenolysis of DMDS with hydrogen.

BACKGROUND OF THE INVENTION

Methionine is one of the human body's essential amino acids and is widely used as an additive for animal feed. It is also used as a starting material for pharmaceutical products. Methionine acts as a precursor for compounds such as choline (lecithin) and creatine. It is also a synthesis starting material for cysteine and taurine.

S-Adenosyl-L-Methionine (SAM) is a derivative of L-Methionine and is involved in the synthesis of various neurotransmitters in the brain, L-Methionine and/or SAM inhibit(s) the accumulation of lipids in the body and improves blood circulation in the brain, heart and kidneys. L-Methionine may also be used to aid digestion, detoxification and excretion of toxic substances or heavy metals such as lead. It has an anti-inflammatory effect on bones and joint diseases and is also an essential nutrient for the hair, thereby preventing the premature undesired loss thereof.

Methionine is already known to be prepared industrially by chemical routes from petrochemical-derived starting materials, as described for example in the documents FR2903690, WO2008006977, US2009318715, U.S. Pat. No. 5,990,349, JP19660043158 and WO9408957. Aside from the fact that these preparation processes do not fall within a process of sustainable development, these chemical routes have the drawback of producing an equal mixture of the two L and D enantiomers.

Completely biological syntheses by bacterial fermentation have been proposed in the literature, with the advantage of only producing the L enantiomer of methionine, as described for example in documents WO07077041, WO09043372, WO10020290 and WO10020681. Nonetheless, the absence of large-scale industrial implementation to date leads to the assumption that the performance and/or cost price of these processes remain unsatisfactory.

Mixed chemical/biological processes have recently been successfully industrialized jointly by the company CJ Cheil-Jedang and the applicant, in which an L-methionine precursor is produced by bacterial fermentation and then reacts enzymatically with methyl mercaptan to produce L-methionine exclusively (cf, WO2008013432 and/or WO2013029690). While these processes have high levels of performance, they require the on-site synthesis of methyl mercaptan, which in turn requires the synthesis of hydrogen by steam methane reforming, the synthesis of hydrogen sulfide by hydrogenation of sulfur and the synthesis thereof from methanol and hydrogen sulfide; that is to say, very large equipment which is not very compatible with industrial extrapolation on a more modest scale in terms of annual production than that which already exists.

There therefore remains a need to produce L-methionine by a mixed process in which the equipment required for the synthesis of methyl mercaptan is smaller than for a synthesis starting from hydrogen, hydrogen sulfide and methanol. It is within this perspective that the present invention comes.

Indeed, the present invention proposes replacing methyl mercaptan in the process summarized below (WO2008013432 and/or WO2013029690) with dimethyl disulfide (DMDS):

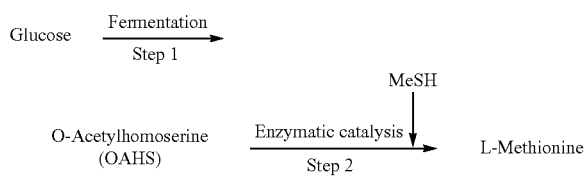

Here, methyl mercaptan (MeSH) is used directly in the second step. The present invention proposes substituting methyl mercaptan with the product of the enzymatic hydrogenolysis of dimethyl disulfide in a prior step or combining everything in a "one pot" reaction, in which glucose and DMDS produce L-methionine.

The following elements can be found in the prior art in relation to the synthesis of methyl mercaptan from dimethyl disulfide.

Patent application EP0649837 proposes a process for the synthesis of methyl mercaptan by catalytic hydrogenolysis, with transition metal sulfides, of dimethyl disulfide with hydrogen. Although this process is efficient, it requires relatively high temperatures of the order of 200° C. to obtain industrially advantageous levels of productivity.

Those skilled in the art also know that it is possible to prepare methyl mercaptan by acidification of an aqueous solution of sodium methyl mercaptide ($CH_3SNa$). This method has the major drawback of producing large amounts of salts, such as sodium chloride or sodium sulfate, depending on whether hydrochloric acid or sulfuric acid is used. These saline aqueous solutions are often very difficult to treat and the traces of foul-smelling products which remain mean that this method cannot be readily envisaged on the industrial scale.

SUMMARY OF THE INVENTION

It has now been found that it is possible to prepare methyl mercaptan by enzymatic reduction of dimethyl disulfide (DMDS) during a step prior to the synthesis of the L-methionine and it has also been found, surprisingly, that it is possible to carry out this enzymatic reduction of DMDS during the synthesis of the L-methionine.

Thus, a subject-matter of the present invention is a process for the preparation of L-methionine similar to that proposed in international applications WO2008013432 and/or WO2013029690 and which makes it possible to dispense with, or at the very least to reduce, the handling of methyl mercaptan, by generating said methyl mercaptan in a reaction for the enzymatic catalysis of DMDS, just before the use of said methyl mercaptan in the synthesis of methionine, or by generating said methyl mercaptan in a reaction for the enzymatic catalysis of DMDS in situ in the reactor for the synthesis of L-methionine.

More particularly, a first subject-matter of the present invention is the process for the preparation of L-methionine, comprising at least the steps of
a) preparation of a mixture comprising:
1) dimethyl disulfide (DMDS),
2) a catalytic amount of amino acid bearing a thiol group or of a thiol-group-containing peptide,
3) a catalytic amount of enzyme catalysing the reaction for the reduction of the disulfide bridge of said amino acid bearing a thiol group or of said thiol-group-containing peptide,
4) hydrogen,
5) a catalytic mount of enzyme catalysing the reaction for the reduction of hydrogen,
6) a catalytic amount of a cofactor common to the two enzymes of the catalytic system (dehydrogenase and reductase),
b) carrying out the enzymatic reaction to form the methyl mercaptan ($CH_3$—SH),
c) addition of a precursor of L-methionine and conversion of said precursor with the methyl mercaptan formed in step b), and
d) recovery and optional purification of the L methionine formed.

The components of step a) above may be added in different orders (the order of addition in step a) is not restrictive). In one embodiment of the invention, the amino acid bearing a thiol group and/or the peptide bearing a thiol group may be in the form of the disulfide of said amino acid and/or of said peptide, respectively, for example glutathione in the form of glutathione disulfide.

BRIEF DESCRIPTION OF THE FIGURES

FIG. 1: Reduction of glutathione/glutathione reductase complex regenerated by the hydrogen.
FIG. 2: Preparation of L-methionine from an L-methionone precursor, dimethyl disulfide, and hydrogen.

DETAILED DESCRIPTION OF THE INVENTION

Generally speaking, the enzyme catalysing the reduction of the disulfide bridge created between two equivalents of said amino acid bearing a thiol group or of said thiol-group-containing peptide is a reductase enzyme. The term "reductase" is used in the remainder of the description for the explanation of the present invention. Similarly, the enzyme catalysing the reaction of reduction of hydrogen is generally referred to as hydrogen dehydrogenase, the term "dehydrogenase" being chosen in the remainder of the description for the explanation of the present invention.

Among the cofactors common to the two enzymes catalysing the reduction and the dehydrogenation (reductase and dehydrogenase), mention may be made, by way of non-limiting examples, of flavinic cofactors and nicotinic cofactors. Preference is given to using nicotinic cofactors and more particularly nicotinamide adenine dinucleotide (NAD), or better still nicotinamide adenine dinucleotide phosphate (NADPH). The cofactors listed above are advantageously used in their reduced forms (for example NADPH, H+) and/or their oxidized forms (for example NADP+), that is to say that they may be added in the reduced and/or oxidized forms into the reaction medium.

The organisation and the order of the additions of the components 1) to 6) in step a) may be carried out in different ways. The enzymatic reaction of step b) is triggered by the addition of one of the components of the catalytic system of the mixture of step a): either an enzyme, or one of the compounds added in a stoichiometric amount (disulfide or organic reducing compound), or one of the compounds added in a catalytic amount (amino acid bearing a thiol group or thiol-group-containing peptide or disulfide corresponding to said thiol or to said peptide or else the cofactor).

Thus, and according to one embodiment of the invention, the process for the preparation of L-methionine comprises at least the steps of:
a') preparation of a mixture comprising:
dimethyl disulfide (DMDS),
a catalytic amount of amino acid bearing a thiol group or of a thiol-group-containing peptide,
a catalytic amount of reductase enzyme corresponding to said amino acid bearing a thiol group or to said thiol-group-containing peptide,
a catalytic amount of NADPH,
b') addition of hydrogen with a catalytic amount of hydrogen dehydrogenase enzyme,
c') carrying out the enzymatic reaction to form methyl mercaptan ($CH_3$—SH),
d') conversion of an L-methionine precursor with the methyl mercaptan formed in step c'), and
e') recovery and optionally purification of the L-methionine formed.

According to the process of the invention, the methyl mercaptan, generally formed in the gaseous state, is then directly placed in contact with a methionine precursor as described below.

The process for the synthesis of L-methionine according to the invention is first and foremost based on the enzymatic reduction of dimethyl disulfide with hydrogen, according to the following reaction:

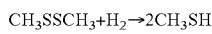

$$CH_3SSCH_3 + H_2 \rightarrow 2CH_3SH$$

It has now been discovered that this reaction is readily catalysed by the enzymatic system employing a thiol-group-containing amino acid or a thiol-group-containing peptide, for example glutathione, in the form of an (amino acid or peptide)/corresponding reductase enzyme complex, regenerated by hydrogen, as described in the appended FIG. 1.

Thus, according to the illustration in FIG. 1, the peptide (the example represented being glutathione) reduces the dimethyl disulfide to methyl mercaptan by converting into a peptide with a disulfide bridge (glutathione disulfide represented). The reductase enzyme (glutathione reductase represented, EC 1.8.1.7 or EC 1.6.4.2) regenerates the peptide (glutathione) and this same enzyme is regenerated by a redox enzymatic complex well known to those skilled in the art, for example the NADPH/NADP+ (nicotinamide adenine dinucleotide phosphate (reduced form and oxidized form)) complex. NADP+ is in turn regenerated to NADPH by means of the dehydrogenase "hydrogen" enzyme EC 1.12.1.5) by virtue of hydrogen The proton released by the hydrogen does not accumulate as it reacts with the glutathione reductase which gave HS—R—S$^-$ after reaction with NADPH and the mercaphide function formed becomes a mercaptan function.

According to a most particularly suited embodiment, the glutathione/glutathione disulfide system combined with the glutathione reductase enzyme makes it possible according to the present invention to reduced the DMDS to methyl mercaptan.

Glutathione is a tripeptide widely used in biology. In reduced form (glutathione) or oxidized form (glutathione disulfide), this species forms an important redox couple in cells. Thus, glutathione is vital for eliminating heavy metals from organisms Thus, for example, application WO05107723 describes a formulation in which glutathione is used to form a chelating preparation and patent U.S. Pat. No. 4,657,856 teaches that glutathione also makes it possible to break down peroxides such as $H_2O_2$ into $H_2O$ via glutathione peroxidase. Finally, glutathione also makes it possible to reduce disulfide bridges present in proteins (Rona Chandrawati, "Triggered Cargo Release by Encapsulated Enzymatic Catalysis in Capsosomes", *Nano Lett.*, (2011), vol. 11, 4958-4963).

According to the process of the invention, a catalytic amount of amino acid bearing a thiol group or of a thiol-group-containing peptide is used to produce methyl mercaptan from dimethyl disulfide.

Among the amino acids bearing a thiol group which may be used in the process of the present invention, mention may be made by way of nonlimiting examples of cysteine and homocysteine. In these cases, the redox enzymatic systems, used which can regenerate the catalytic cycle in the same way as the system cysteine/cystine reductase EC 1.8.1.6 and homocysteine/homocysteine reductase.

It may be advantageous to use homocysteine since this amino acid can be prepared from OAHS (L-methionine precursor), hydrogen sulfide ($H_2S$) and the enzyme catalysing the reaction leading to methionine. Thus, a very small amount of $H_2S$ in the reaction medium creates, in situ, the equivalent cycle to that of glutathione.

Among the peptides bearing a thiol group which may be used in the process of the present invention, mention may be made by way of nonlimiting examples of glutathione and thioredoxin. The glutathione/glutathione reductase system described above may thus be replaced by the thioredoxin (CAS No. 52500-60-4)/thioredoxin reductase (EC 1.8.1.9 or EC 1.6.4.5) system.

Glutathione and the glutathione/glutathione reductase system are most particularly preferred for the present invention, due to the costs of these compounds and the ease with which they are procured.

In the process according to the invention, the hydrogen can be added to the reaction medium according to any means known to those skilled in the art, for example via bubbling into the reaction medium, which is advantageously an aqueous-organic reaction medium. The hydrogen pressure in the reactor corresponds to the pressure of the reaction medium itself which is defined hereinafter.

The enzyme used is the hydrogen dehydrogenase enzyme, which is also well known to those skilled in the art.

In the process according to the invention, in the case in which the enzymatic reduction of the DMDS is carried out in a separate reactor to the synthesis of the L-Methionine, only the DUDS and the hydrogen are used in a stoichiometric amount and all the other components (glutathione, cofactor (for example NADPH) and the 2 enzymes) are used in catalytic amounts. In the case in which the enzymatic reduction reaction of the DMDS is carried out with the synthesis of the L-methionine in a single reactor ("one pot"), the L-methionine precursor is also added in a stoichiometric amount, while the supplemental reagents for this synthesis such as pyridoxal phosphate (PLP) and the enzyme specific to this reaction are added in catalytic amounts.

The preferred concentrations of pyridoxal phosphate and of enzyme specific to the precursor are those that can be found in international applications WO2008013432 and/or WO2013029690.

The advantages brought about by the synthesis of methyl mercaptan from dimethyl disulfide by enzymatic catalysis are numerous, whether in the case of 2 successive steps or of the "one pot" process. Among these advantages, mention may be made of the possibility of working in aqueous or aqueous-organic solution, under very mild temperature and pressure conditions and under pH conditions close to neutrality. All these conditions are typical of a "green" or "sustainable" process, and are entirely compatible with the preparation of L-methionine as described in international applications WO2008013432 and/or WO2013029690.

Another advantage when the process uses dimethyl disulfide is that the methyl mercaptan produced, which is in the gaseous state under the reaction conditions, leaves the reaction medium as it is formed, optionally accompanied by arty unreached hydrogen. It can therefore be used directly upon leaving the reactor in an application further downstream if the unreacted hydrogen does not adversely affect the latter.

The methyl mercaptan may therefore be directly used, upon leaving the reactor, in the synthesis of the L-methionine, as described for example in WO2008013432 and/or WO2013029690, that is to say for example from O-acetyl-homoserine or O-succinyl-homoserine and enzymes such as O-acetyl-homoserine sulfhydrylase or O-succinyl-homoserine sulfhydrylase, respectively.

In the opposite case, those skilled in the art would easily be able to separate the unconverted hydrogen from the methyl mercaptan. The methyl mercaptan can also be readily liquefied cryogenically for example, if it is desired to isolate or separate it.

The outlet gases containing hydrogen and methyl mercaptan may, if desired and if necessary, be recycled into the first reactor (enzymatic reduction of DMDS) after passing into the second reactor (L-methionine synthesis) if the methyl mercaptan has not been completely converted to L-methionine. The process according to the invention therefore describes a process for the synthesis of L-methionine in 2 successive enzymatic steps from an L-methionine precursor and DMDS.

It is also possible to carry out the synthesis of L-methionine in one and the same reactor. In this case, all the reagents necessary for the synthesis of the L-methionine are added to the system for the enzymatic reduction of the DMDS (step a) above) and the reactor is dosed to avoid loss of the methyl mercaptan formed by in situ enzymatic reduction of the DMDS. The methyl mercaptan then reacts with the L-methionine precursor to give L-methionine. The process according to the present invention therefore describes a process for the direct synthesis of L-methionine from an L-methionine precursor and DMDS, as illustrated by the appended FIG. 2, i.e. the synthesis from OAHS, DMDS and hydrogen.

The dimethyl disulfide (DMDS) may be produced at another site from methyl mercaptan and an oxidizer such as oxygen, sulfur or aqueous hydrogen peroxide solution, for example, or else from dimethyl sulfate and sodium disulfide. The DMDS may also originate from a source of disulfide oils (DSO), purified for example by reactive distillation as described in application WO2014033399.

The reduction of DMDS by enzymatic catalysis may be considered as a process which makes it possible to avoid transporting methyl mercaptan from its site of production by existing industrial routes, to its site of use, if they are different. Indeed, methyl mercaptan is a toxic and extremely foul-smelling gas at room temperature, which significantly complicates its transportation, which is already heavily regulated unlike DMDS. Thus, DMDS can therefore be used to produce methyl mercaptan directly on the site of use of the latter in the synthesis of L-methionine, thereby further reducing the drawbacks linked to the toxicity and odour of this product, and also the industrial risks linked to it.

In the case of the synthesis process in 2 successive steps, since the DMDS is consumed in the reaction and the methyl mercaptan leaves the reaction medium as it is formed, with or without unconverted hydrogen, no product accumulates if it is assumed that hydrogen and DMDS are fed continuously. It is therefore unnecessary to recycle the catalytic system in light of the products entering and leaving the reactor.

According to one embodiment, the process according to the invention comprises the preparation of methyl mercaptan by enzymatic reduction of DMDS, then reaction of said methyl mercaptan formed with an L-methionine precursor to give L-methionine. In this case, the process according to the invention comprises at least the following steps:

Step 1: preparation of an l-methionine precursor, for example by bacterial fermentation of glucose (cf. WO2008013432 and/or WO2013029690), Step 2: enzymatic reduction of DMDS in a reactor R1 with formation of methyl mercaptan, and optionally unconverted hydrogen, leaving said reactor R1 (steps a) to c) above), Step 3: enzymatic synthesis of l-methionine in a reactor R2 with the precursor from step 1 and the methyl mercaptan from step 2 (step d) above), Step 4 (optional): recycling of the unconverted hydrogen to step 2 and recycling of the methyl mercaptan to step 2 or 3, and Step 5: recovery and optionally purification of the l-methionine formed (step e) above).

For step 1, the range of conditions which can be used will be found in international applications WO2008013432 and/or WO2013029690.

For step 2, the reaction temperature is within a range extending from 10° C. to 50° C., preferably between 15° C. and 45° C., more preferably between 20° C. and 40° C.

The pH of the reaction may be between 5 and 9, preferably between 6 and 8.5, more preferably still between 6 and 8, and most particularly preferably between 7.0 and 8.0. Entirely preferably, the pH of a medium buffered to a pH value of between 7.5 and 8.0 will be chosen. According to another preferred embodiment, the pH of a medium buffered to a ph value of between 6.5 and 7.5 is chosen.

The pressure used for the reaction may range from a reduced pressure compared to atmospheric pressure to several bar (several hundred kPa), depending on the reagents and equipment used. Preferably, use will be made of a pressure ranging from atmospheric pressure to 20 bar (2 MPa) and even more preferably the process will be carried out under a pressure ranging from atmospheric pressure to 3 bar (300 kPa).

For step 3, reference will be made to international application WO2013029690for the ideal conditions.

According to another embodiment (another variant), the process according to the present invention is carried out in one and the same reactor ("one pot") and in this case comprises at least the following steps:

Step 1': Step preparation of an L-methionine precursor, for example by bacterial fermentation, in particular but non-limitingly of glucose fermentation (similar to step 1 above), Step 2': enzymatic reduction of DMDS in a reactor R1 with in situ formation of methyl mercaptan and concomitant enzymatic synthesis of l-methionine in the same reactor with the precursor obtained in step 1', Step 3' (optional): recycling loop of the hydrogen and methyl mercaptan in the reactor R1, at step 2', and Step 4'; recovery and optionally purification of the L-methionine formed (step e) above).

For step 1', the range of conditions which can be used will be found in the international applications WO2008013432 and/or WO2013029690.

For step 2', the operating conditions are as follows.

The reaction temperature is within a range extending from 10° C. to 50° C., preferably from 15° C. to 45° C., more preferably from 20° C. to 40° C.

The pH of the reaction is advantageously between 6 and 8, preferably between 6.2 and 7.5. Entirely preferably, the reaction is carried out at the pH of the 0.2 mol.l$^{-1}$ phosphate buffer and equal to 7.0.

Preferably, the pressure used for the "one pot" reaction can range from a pressure that is reduced with respect to atmospheric pressure to several bar (several hundred kPa), depending on the reagents and material used. Preferably, a pressure ranging from atmospheric pressure to 20 bar (2 MPa) will be used and even more preferably the process will be performed at a pressure ranging from atmospheric pressure to 3 bar (300 kPa).

The DMDS/L-methionine precursor molar ratio is between 0.1 and 10, generally between 0.5 and 5, and preferably the molar ratio is stoichiometry (molar ratio=0.5) but may be higher if this proves beneficial to the reaction kinetics.

In one or the other of the variants of the process according to the invention, the process can be carried out batchwise or continuously, in a glass or metal reactor depending on the operating conditions selected and the reagents used. According to one embodiment, the process of the invention is a semi-continuous process in which hydrogen is added as it is consumed in the reaction.

In one or the other of the variants of the process according to the invention, the ideal hydrogen/DMDS molar ratio is stoichiometry (molar ratio=1) but may vary from 0.01 to 100, if those skilled in the art find any benefit therein, such as continuous addition of the hydrogen while the DMDS is introduced from the start into the reactor. Preferably, this molar ratio is chosen between 1 and 20 overall, over the whole of the reaction.

Any unconverted hydrogen can be recycled from the outlet of the reactor to the inlet until it is exhausted completely. Consideration may also be given to a loop with hydrogen and methyl mercaptan, until the hydrogen has completely converted the DMDS. In this configuration the outlet gases from the reactor R2 (or from the reactor, in the case where the reaction is performed in "one pot") contain virtually exclusively methyl mercaptan.

The elements present in catalytic amounts in the mixture prepared in step a) above (amino acid bearing a thiol group or a thiol-group-containing peptide, or else disulphide corresponding to said amino acid or to said peptide, reductase enzyme, dehydrogenase enzyme, cofactor (for example NADPH)) are easily available commercially or can be prepared according to techniques well known to those skilled in the art. These different elements may be in solid or liquid form and may very advantageously be dissolved in water to be used in the process of the invention. The enzymes used may also be grafted onto a support (in the case of supported enzymes).

The aqueous solution of enzymatic complex comprising the amino acid or the peptide may also be reconstituted by methods known to those skilled in the art, for example by permeabilization of cells which contain these elements. This aqueous solution, a composition of which is given in the following Example 1, may be used in contents by weight of between 0.01% and 20% relative to the total weight of the reaction medium. Preferably, a content of between 0.5% and 10% will be used.

The preferred concentrations of pyridoxal phosphate and of enzyme specific to the L-methionine precursor are those that can be found in international applications WO2008013432 and/or WO2013029690.

The invention will be better understood with the following examples nonlimiting relative to the scope of the invention. All the tests presented below were carried out under anaerobic conditions.

EXAMPLES

Example 1

Process in 2 Successive Steps 10 ml of glutathione enzymatic complex (Aldrich) are introduced into a reactor R1 containing 150 ml of aqueous solution buffered to pH 7.8. The solution of enzymatic complex contains: 185 mg (0.6 mmol) of glutathione, 200 U of glutathione reductase, 50 mg (0.06 mmol) of NADPH and 200 U of hydrogen dehydrogenase enzyme. The reaction medium is brought to 35° C. with mechanical stirring. A first sample is taken at t=0, Subsequently, the dimethyl disulfide (9.4 g, 0.1 mol) is placed in a burette and added dropwise to the reactor.

At the same time, a 4 $L.h^{-1}$ stream, of hydrogen (measured under normal temperature and pressure conditions) is introduced into the reactor via bubbling. The reaction is carried out at atmospheric pressure.

Gas chromatography analysis of the gases leaving the reactor shows virtually essentially the presence of hydrogen and methyl mercaptan (some traces of water), The DMDS and the hydrogen (hydrogen/DMDS molar ratio over the, whole of the reaction=10.7) are introduced in 6 hours and a final gas chromatography analysis of the reaction medium confirms the absence of methyl mercaptan which has been driven out of the reactor by the excess hydrogen. These outlet gases from the reactor R1 are sent directly into the reactor R2.

In parallel, 5 g of O-acetyl-L-homoserine (OAHS) (the O-acetyl-L-homoserine was synthesized from L-homoserine and acetic anhydride as per Sadamu Nagai, "*Synthesis of O-acetyl-L-homoserine*", Academic Press, (1971), vol. 17, pp. 423-424) are introduced into the second reactor R2 containing 75 ml of 0.1 $mol.l^{-1}$ phosphate buffer at pH 6.60. The solution is brought to 35° C. with mechanical stirring.

Before the reaction starts, a sample (t=0) of 1 ml of the reaction medium is taken. A solution of pyridoxal phosphate (10 mmol. 0.4 g) and the enzyme O-acetyl-L-homoserine sulfhydrylase (0.6 g) are dissolved in 10 ml of water then added to the reactor The methyl mercaptan is introduced via the reaction of the reactor R1 and advantageously propelled by the excess hydrogen, or else when the hydrogen is in stoichiometric or substoichiometric, conditions with respect to the DMDS the methyl mercaptan is advantageously propelled by a stream of inert gas, for example a nitrogen stream. The reaction then begins. The formation of L-methionine and the disappearance of OAHS are monitored by HPLC. The outlet gases from the reactor R2 are trapped in a 20% aqueous sodium hydroxide solution. The analyses show that the OAHS has been converted to a degree of 52% into L-methionine and that the excess DMDS has been converted into methyl mercaptan found in the sodium hydroxide trap.

Example 2

"One Pot" Process 10 ml of the enzymatic complex, 5 g (31 mmol) of O-acetyl-L-homoserine (OAHS the O-acetyl-L-homoserine was synthesized from L-homoserine and acetic anhydride as per Sadamu Nagai, "Synthesis of O-acetyl-l-homoserine", Academic Press, (1971), vol. 17, pp. 423-424) are introduced into a reactor containing 150 ml of 0.2 $mol.l^{-1}$ phosphate buffer at pH 7. The solution of the enzymatic complex contains: 185 mg (0.6 mmol) of glutathione, 200 U of glutathione reductase, 50 mg (0.60 mmol) of NADPH, 200 U of hydrogen dehydrogenase enzyme, 0.4 g (1.6 mmol) of pyridoxal phosphate and 0.6 g of O-acetyl-L-homoserine sulfhydrylase.

The reaction medium is brought to 35° C. with mechanical stirring. A first sample at t=0 is taken. Subsequently, the dimethyl disulfide (3 g, 32 mmol) is placed in a burette and added dropwise and a flow of 4 litres/h of hydrogen is introduced; the reaction begins The reaction is monitored by HPLC to see the disappearance of the OAHS and the formation of the L-methionine. After 6 hours, 12% of the OAHS has been converted into L-methionine, demonstrating the possibility of producing L-methionine by a "one pot" process from an L-methionine precursor, DMDS and hydrogen.

Example 3

"One Pot" Process 10 ml of the enzymatic complex, 5 g (31 mmol) of O-acetyl-L-homoserine (OAHS—the O-acetyl-L-homoserine was synthesized from L-homoserine and acetic anhydride as per Sadamu Nagai, "Synthesis of O-acetyl-L-homoserine", Academic Press, (1971), vol. 17, pp. 423-424) are introduced into a reactor containing 70 ml of 0.1 $mol.l^{-1}$ phosphate buffer at pH 6.8.

The solution of the enzymatic complex contains: 200 mg (0.65 mol) of glutathione, 500 U of glutathione reductase, 100 mg (0.13 mol) of NADPH, 50 U of hydrogen dehydrogenase, 400 mg (1.6 mmol) of pyridoxal phosphate, 2 g of O-acetyl-L-homoserine and 0.6 g of O-acetyl-L-homoserine sulfhydrylase.

The hydrogen dehydrogenase is obtained from the culture of microorganisms (according to Biller et al., "Fermentation Hyperthermophiler Mikroorganismen am Beispiel von *Pyrococcus Furiosus*", Shaker Verlag, Maastricht/Herzogenrath, 2002), using techniques well known to those skilled in the art.

The reaction medium is brought to 35° C. with mechanical stirring and nitrogen flushing. A first sample is taken at t=0. Subsequently, 20 g (0.22 mol) of dimethyl disulfide are added by means of a syringe. At the same time, 4 $l.h^{-1}$ of hydrogen (measured under standard conditions of temperature and pressure) are introduced by bubbling into the reaction medium. The reaction started in this way is carried out at atmospheric pressure for 18 hours. The reaction is monitored by HPLC to see the disappearance of the OAHS and the formation of L-methionine. At the end of the reaction, 27% of the OAHS has been converted into L-methionine, demonstrating the possibility of producing L-methionine by a "one pot" process from an L-methionine precursor, DMDS and hydrogen.

The invention claimed is:
1. A process for the preparation of L-methionine, comprising:
   (a) preparing a mixture, comprising:
      (1) dimethyl disulfide (DMDS),
      (2) a catalytic amount of an amino acid bearing a thiol group or of a thiol-group-containing peptide, wherein the amino acid bearing a thiol group or the thiol-group-containing peptide may optionally be in the form of the corresponding disulfide,
      (3) a catalytic amount of a reductase enzyme catalyzing the reaction for the reduction of a disulfide bridge of the amino acid bearing a thiol group or of the thiol-group-containing peptide,
      (4) hydrogen,
      (5) a catalytic amount of a dehydrogenase enzyme catalyzing the reaction for the reduction of hydrogen, and
      (6) a catalytic amount of a cofactor common to the reductase and the dehydrogenase,
   (b) carrying out the enzymatic reaction to form methyl mercaptan ($CH_3$—SH),
   (c) adding a precursor of L-methionine and reacting the precursor with the methyl mercaptan formed in (b) to produce L-methionine, and
   (d) recovering and, optionally, purifying the L-methionine.
2. The process of claim 1, comprising:
   (a') preparing a mixture, comprising:
      dimethyl disulfide (DMDS),
      a catalytic amount of amino acid bearing a thiol group or of a thiol-group-containing peptide, wherein the amino acid bearing a thiol group or the thiol-group-containing peptide may optionally be in the form of the corresponding disulfide,
      a catalytic amount of a reductase enzyme corresponding to the amino acid bearing a thiol group or to the thiol-group-containing peptide, and
      a catalytic amount of NADPH,
   (b') adding hydrogen with a catalytic amount of a hydrogen dehydrogenase enzyme,
   (c') carrying out the enzymatic reaction to form methyl mercaptan ($CH_3$—SH),
   (d') converting an L-methionine precursor with the methyl mercaptan formed in (c') to produce L-methionine, and
   (e') recovering and, optionally, purifying the L-methionine.
3. The process of claim 1, wherein the methyl mercaptan is directly placed in contact with the precursor of L-methionine.
4. The process of claim 1, wherein the amino acid bearing a thiol group or the peptide bearing a thiol group is chosen from cysteine, homocysteine, glutathione and thioredoxin.

5. The process of claim 1, wherein the L-methionine precursor is chosen from O-acetyl-L-homoserine and O-succinyl-L-homoserine.
6. The process of claim 1, in which hydrogen is added to the reaction medium via bubbling.
7. The process of claim 1, comprising preparing methyl mercaptan by enzymatically reducing the DMDS, then reacting the methyl mercaptan with an L-methionine precursor to produce L-methionine.
8. The process according of claim 7, comprising:
   (1) preparing an L-methionine precursor,
   (2) enzymatically reducing DMDS in a first reactor with formation of methyl mercaptan, and, optionally, unconverted hydrogen, leaving the first reactor,
   (3) enzymatically synthesizing L-methionine in a second reactor with the L-methionine precursor from (1) and the methyl mercaptan from (2),
   (4) optionally, recycling of the unconverted hydrogen to (2) and recycling the methyl mercaptan to (2) or (3), and
   (5) recovering and, optionally, purifying the L-methionine.
9. The process of claim 1, wherein the synthesis of methyl mercaptan from DMDS and the synthesis of L-methionine from the methyl mercaptan are carried out in one and the same reactor.
10. The process of claim 9, comprising:
    (1') preparing an L-methionine precursor,
    (2') enzymatically reducing DMDS in a first reactor with in situ formation of methyl mercaptan and concomitant enzymatic synthesis of L-methionine in the same reactor with the precursor obtained in (1'),
    (3') optionally, recycling loop of the hydrogen and methyl mercaptan in the first reactor, at (2'), and
    (4') recovering and, optionally, purifying the L-methionine.
11. The process of claim 1, which is carried out batchwise or continuously.
12. The process of claim 1, wherein the hydrogen/DMDS molar ratio varies from 0.01 to 100 over the whole of the reaction.
13. The process of claim 1, wherein the hydrogen/DMDS molar ratio varies from 1 to 20 over the whole of the reaction.
14. The process of claim 1, wherein the DMDS/L-methionine precursor molar ratio is between 0.1 and 10.
15. The process of claim 1, wherein the DMDS/L-methionine precursor molar ratio is between 0.5 and 5.
16. The process of claim 1, wherein the reaction temperature is within a range extending from 10° C. to 50° C.
17. The process of claim 1, wherein the reaction temperature is within a range extending from 15° C. to 45° C.
18. The process of claim 1, wherein the reaction temperature is within a range extending from 20° C. to 40° C.
19. The process of claim 1, wherein the amino acid bearing a thiol group or a thiol-group-containing peptide is glutathione.
20. The process of claim 1, wherein the cofactor is NADPH.

* * * * *